United States Patent [19]

Klaas

[11] Patent Number: 5,630,821

[45] Date of Patent: May 20, 1997

[54] APPARATUS FOR IMPLANTING AN INTRAOCULAR LENS

[76] Inventor: Dieter Klaas, Bahnhofstrasse 5, D-86316 Friedberg, Germany

[21] Appl. No.: 420,007

[22] Filed: Apr. 11, 1995

[30] Foreign Application Priority Data

Feb. 20, 1995 [DE] Germany ............ 195 05 761.9

[51] Int. Cl.⁶ ............ A61F 9/00; A61B 17/28
[52] U.S. Cl. ............ 606/107; 606/205; 606/207; 606/210
[58] Field of Search ............ 606/107, 205, 606/206, 207, 209, 210

[56] References Cited

U.S. PATENT DOCUMENTS

| D. 275,790 | 10/1984 | Marlowe | 606/207 |
|---|---|---|---|
| 1,275,414 | 8/1918 | Forbes | 606/209 |
| 1,422,538 | 7/1922 | Cameron | 606/207 |
| 3,648,701 | 3/1972 | Botts | 606/209 |
| 4,164,223 | 8/1979 | Munib | 606/209 |
| 4,165,746 | 8/1979 | Burgin | 606/207 |
| 4,287,890 | 9/1981 | Fogarty | 606/209 |
| 4,452,244 | 6/1984 | Chin | 606/209 |
| 4,580,567 | 4/1986 | Schweitzer et al. | 606/207 |
| 4,896,661 | 1/1990 | Bogert et al. | 606/207 |

FOREIGN PATENT DOCUMENTS

| 3600789 | 7/1987 | Germany | 606/209 |
|---|---|---|---|
| 278763 | 2/1952 | Switzerland | 606/209 |

Primary Examiner—Robert A. Hafer
Assistant Examiner—Benjamin Koo
Attorney, Agent, or Firm—Keck, Mahin & Cate

[57] ABSTRACT

An apparatus for implanting an intraocular lens comprises two gripping elements, the front ends of which carry contact elements which are movable towards each other with the gripping elements so that the lens to be implanted can be held therebetween. At least one of the contact elements is mounted rotatably on the respective gripping element.

22 Claims, 2 Drawing Sheets

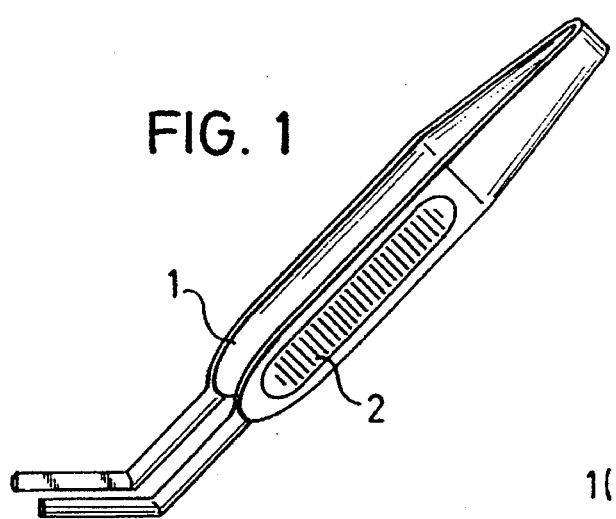
FIG. 1
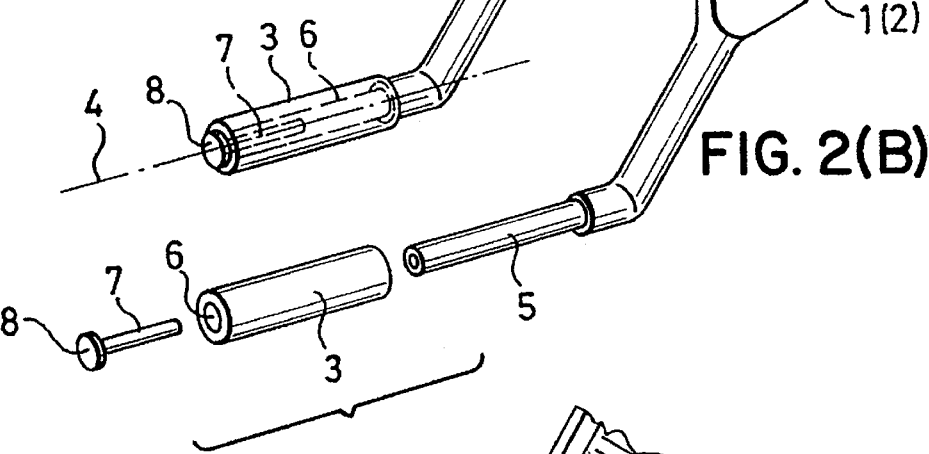
FIG. 2(A)
FIG. 2(B)
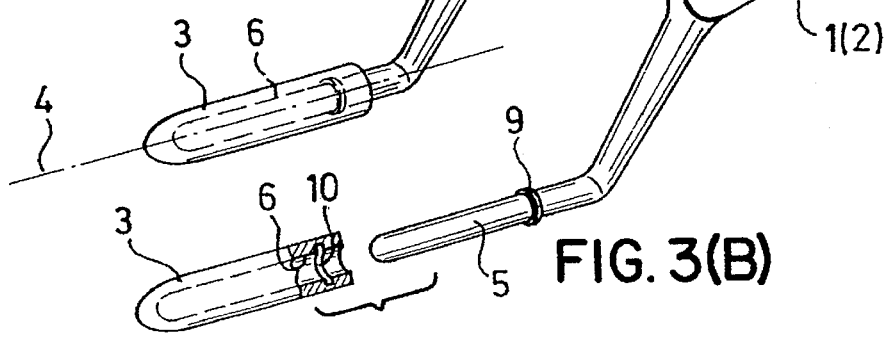
FIG. 3(A)
FIG. 3(B)

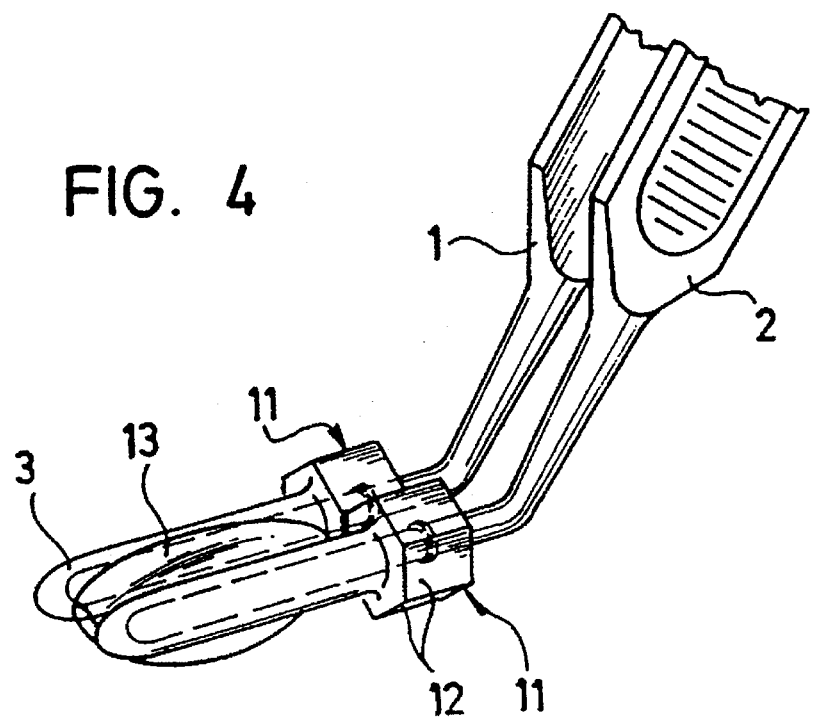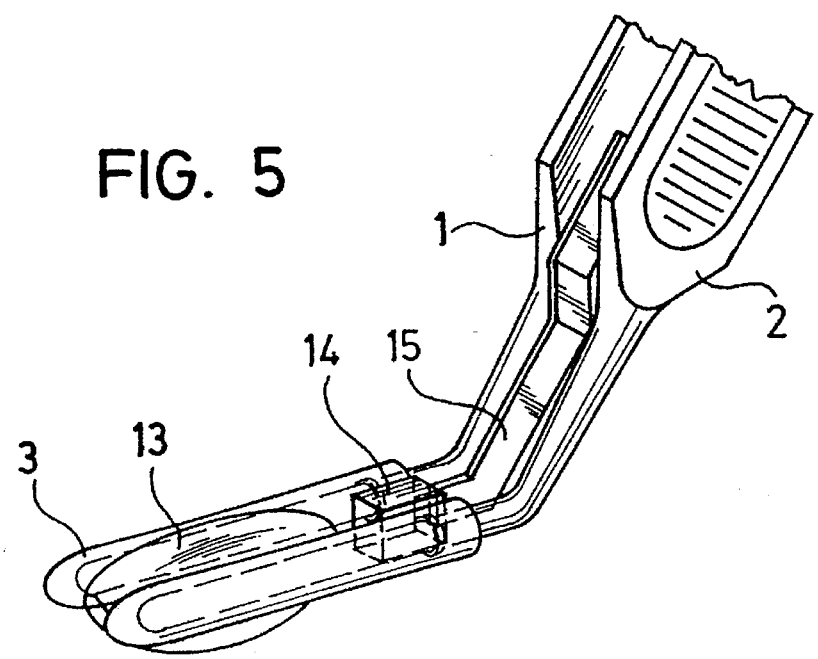

APPARATUS FOR IMPLANTING AN INTRAOCULAR LENS

BACKGROUND OF THE INVENTION

One form of apparatus for implanting an intraocular lens, as is to be found in U.S. Pat. No. 4,844,065, comprises two gripping elements, the front ends of which constitute contact elements which are movable towards each other for holding the lens to be implanted therebetween. The front ends of the gripping elements which form the contact elements are provided with widened holding surfaces for the intraocular lens which is to be held in the implantation operation. That arrangement is intended to prevent the lens from being pressed in and permanently deformed, at the portions of the lens surface which are engaged by the contact elements, while at the same time ensuring that the intraocular lens is held securely when it is being fitted into the eye.

Difficulties arise however when, after the intraocular lens has been fitted into the eye, for example into the posterior chamber, the surfaces of the contact elements, which hold the intraocular lens, are to be removed from the surface of the lens. Particularly when dealing with lenses which are implanted in the folded condition, the surface of the lens can adhere strongly to the surfaces of the contact elements so that, when the gripping elements are removed from the eye, the lens subsequently accidentally slips out of its desired position, and subsequent correction of the lens positioning is required.

SUMMARY OF THE INVENTION

An object of the present invention is to provide a lens implantation apparatus in which the lens to be implanted is held securely for the implantation operation but which is easily detachable from the surface of the implanted lens.

In accordance with the invention the foregoing and other objects are attained by an apparatus for implanting an intraocular lens, for example in a folded condition, comprising first and second gripping elements having front ends which are movable towards each other to hold a lens to be implanted, and contact elements of which at least one is mounted rotatably on the respective gripping element at the front end thereof.

The contact element or elements which are mounted rotatably at the front ends of the gripping elements can have rotary mountings which are blocked so as to be non-rotatable, when subjected to a loading from the exterior, by virtue of the existence of frictional forces. When the lens to be implanted is held under a given pressure between the two contact elements, the frictional forces in the rotary mountings increase so that rotary movement of the contact elements is prevented, while the lens is being held. Particularly when a lens is being implanted in a folded condition, a loading is applied to the contact elements, perpendicularly to the axis of rotation of the respective contact element, by the stress which is present in the folded lens, so that the increased frictional forces in the rotary mountings prevent the contact elements from rotating during the implantation operation. The lens is therefore held securely between the two contact elements.

Outside its lens-gripping surface area, one or both contact elements may be of a larger transverse dimension or diameter than the surface region thereof which comes into contact with the intraocular lens to be engaged. That ensures that, when in particular a folded lens is held under pressure, the parts of the contact elements which are of the increased dimension or diameter bear against each other and act as an abutment means to prevent rotary movement of the contact elements. Preferably the respective rearward end of each contact element is of a larger dimension or diameter than the remaining region of the contact element. In the axial direction the peripheral surface of the thickened contact element region may have narrow flat surfaces, wherein two such flat surfaces, which come into contact with each other, of the two contact elements form the desired abutment effect and provide for the blocking action to prevent rotary movement.

After the lens has been fitted into the eye the pressure applied to the gripping elements is released and, when the lens unfolds, the forces applied to the rotary mountings of the contact elements also decrease. When the frictional forces decrease the contact elements can rotate, thereby providing for automatic detachment of the respective contact surface on the contact element from the surface of the lens.

At least one of the two gripping elements is provided at its front end with a contact element which is rotatable in the above-indicated way. The respective contact element can be in the form of a roller. The surface of the roller can be cylindrical, convex or concave. It is also possible for the outside surface of the roller to be of a frustoconical shape.

The surface of the contact element is preferably polished. The contact element can be such that it can be pushed on to the front end of the respective gripping element and can be fixed in the axial direction by an arresting means.

Further objects, features and details of the present invention will be apparent from the following description of preferred embodiments of the invention.

BRIEF DESCRIPTION OF THE DRAWING

FIG. 1 shows an implantation instrument in the form of a pincer arrangement, in accordance with a known design configuration, FIG. 2(A) shows the front end of a gripping element in accordance with a first embodiment of the invention, FIG. 2(B) shows the structure of FIG. 2(A) but in the exploded condition, FIG. 3(A) shows the front end of a gripping element in accordance with a second embodiment of the invention, FIG. 3(B) shows the structure of FIG. 3(A) but in the exploded condition, FIG. 4 shows the front ends of gripping elements of a third embodiment of the invention, and FIG. 5 shows a further embodiment.

DESCRIPTION OF THE PREFERRED EMBODIMENTS

FIG. 1 shows an implantation instrument comprising gripping elements 1 and 2 which are connected together in the form of a pincer arrangement. The front ends of the gripping elements 1 and 2 are angled to serve as contact elements for gripping a lens to be implanted. In the known configuration shown, the inside surfaces of the contact elements are flattened or enlarged in order to ensure that the intraocular lens, in particular a folded intraocular lens, is held securely in the implantation operation.

FIGS. 2(A) and (B) and 3(A) and (B) show first and second embodiments of the invention. These Figures illustrate only the lower and front angled ends of the gripping elements 1 and 2. These embodiments of the invention have contact elements 3 which are mounted rotatably at the front ends of the gripping elements 1 and 2. In the views shown in FIGS. 2(A) and 3(A) the contact elements 3 which are in the form of rollers are shown in the assembled condition while the views in FIGS. 2(B) and 3(B) show the individual parts at the front ends of the gripping elements 1 and 2. The contact elements 3 which are each in the form of a roller have a respective bore 6. With the bore 6, the contact element 3 is pushed on to a mounting pin 5 at the front end of the respective gripping elements 1 and 2. The mounting pin 5 which is fitted into the bore 6 in the contact element 3 in roller form constitutes a rotary mounting for the contact element 3. In the embodiment shown in FIGS. 2(A) and (B) the contact element 3 in roller form is fixed in the axial direction by a holding pin 7 fitted in a bore in the mounting pin 5, with an abutment in the form of a head 8. The fixing action is such that the contact element 3 can rotate on the mounting pin 5.

In the embodiment shown in FIGS. 3(A) and (B) the contact element 3 is fixed in the axial direction by a collar or flange 9 on the mounting pin 5. The flange 9 engages into an annular recess 10 at the wall of the bore 6. In that way the contact element 3 is fixed in the axial direction and can rotate about the axis of rotation 4 relative to the mounting pin 5.

In the embodiment shown in FIGS. 2(A) and (B) the bore 6 is open at both ends, while in the embodiment shown in FIGS. 3(A) and (B) the bore is open only at one end and closed at the front end. The gripping elements 1 and 2, in regard to which at least one of the two gripping elements is provided with a rotatable contact element 3, can be connected together like a pincer arrangement, as is shown in FIG. 1.

When a lens and in particular a folded lens is held between the two contact elements 3, such high frictional forces act between the wall of the bore 6 and the outside surface of the mounting pin 5 that the respective contact element 3 is prevented from rotating. That guarantees that the lens is held securely between the contact elements 3. When the pressure applied by hand to the gripping elements 1 and 2 is released and the lens unfolds, the loading which produces its effect in the rotary mounting, that is to say between the outside surface of the mounting pin 5 and the wall of the bore 6, is also reduced. When the lens unfolds, forces act in a tangential direction on to the outside surface of the contact element 3, and those forces then exceed the frictional forces between the mounting pin 5 and the wall of the bore 6 so that the contact element 3 can rotate. In that situation, the contact surface of the contact element 3 automatically comes away from the surface of the lens.

In the embodiment shown in FIG. 4, the contact elements 3 are of a thickened configuration at their rear ends, thus forming a contact element region 11 which is of enlarged transverse dimension or diameter relative to the region of the contact element 3, in which a lens 13 to be implanted is held. At the peripheral surfaces of the contact element regions 11 of larger diameter, flat narrow surfaces 12 extend parallel to the axis of the contact element 3, those flat narrow surfaces 12 having an abutment or blocking action when they bear against each other. In that way, as in the case of the embodiments shown in FIGS. 2 and 3, in addition to the frictional forces which are operative in the rotary mountings, the abutment action prevents rotary movement of the contact elements 3 when the lens 13 to be implanted is held. When the lens 13 to be implanted is held, the flat surfaces 12 at the peripheral surfaces of the thickened contact element regions 11 are pressed against each other to thus exert the abutment action. That provides for effective blocking of the contact elements 3 to prevent rotary movement thereof when the lens 13 is held.

When the pressure on the 9ripping elements 1 and 2 and thus on the surfaces 12 which bear against each other is reduced and the surfaces 12 which are bearing against each other move away from each other, the lens 13 unfolds, whereupon the contact elements 3 can turn. That provides for effective separation of the lens 13 to be implanted, from the contact elements 3.

The embodiment shown in FIG. 5 also provides that rotary movement of the contact elements is prevented by an abutment action when the lens to be implanted is being held. For that purpose an abutment 14 is provided in the rearward region of the rotatable contact elements 3, between the contact elements 3. The abutment 14 is preferably fixed by way of a spring element, for example a leaf spring 15, to one of the two gripping elements 1 and 2 of the pincer arrangement. In the construction illustrated the abutment 14 is fixed to the gripping element 1. The thickness of the abutment 14 transversely to the axes of rotation, as indicated by reference numeral 4 in FIGS. 2(A) and (B) and 3(A) and (B), of the contact elements 3 is such as to guarantee that the lens to be implanted is securely held, particularly in its folded condition, between the contact elements 3, while at the same time in their rearward regions the two contact elements 3 bear against the side surfaces of the abutment 14 in such a way that rotary movement is prevented. For that purpose additional flat surfaces may be provided in the contact region of the contact elements against the abutment 14, as in the embodiment shown in FIG. 4.

The gripping elements 1, 2 can be in the form of disposable products and can be fitted on to the mounting pins 5.

It is however also possible for the mounting pins 5 with the contact elements 3 mounted rotatably thereon to be in the form of disposable products which, for the purposes of use, are inserted or fitted into the upper parts of the pincer gripping elements 1 and 2.

The entire pincer arrangement can also be in the form of a disposable product.

In particular the contact elements 3 which are in the form of disposable products or the contact elements 3 which are mounted rotatably on the mounting pins 5 and which are in the form of disposable products can be kept in readiness for use, jointly with a folding device as is known from U.S. Pat. No. 5,139,501 to which reference is therefore directed. Particularly in the case of a folding device which is in the form of a storage container, those disposable products are suitable as additional components of the storage container in which the lens, in particular a folded lens, is stored and marketed. The disposable product which is formed as the pincer arrangement can also be used in conjunction with a folding device of such a configuration, in a set.

It will be appreciated that the above-described embodiments of the invention have been set forth only by way of example and illustration of the invention and that various modifications and alterations may be made therein without thereby departing from the spirit and scope of the invention.

What is claimed is:

1. An apparatus for implanting an intraocular lens comprising:

first and second gripping elements having front ends which are movable towards each other for holding the intraocular lens therebetween for implanting;

at least one contact element mounted rotatably on each of the gripping elements; and an abutment disposed adjacent to rearward regions of the contact elements and between the contact elements;

the thickness of the contact elements being such that the intraocular lens is securely held between the contact elements while the rearward regions of the contact elements bear against side surfaces of the abutment so that rotary movement of the contact elements is prevented.

2. An apparatus as set forth in claim 1 wherein each contact element is a roller.

3. An apparatus as set forth in claim 1, wherein said abutment blocks said rotary movement upon a given loading on the contact elements perpendicularly to their axes of rotation.

4. An apparatus as set forth in claim 1 wherein the contact elements are rotatably mounted by cylindrical mounting pins and matching cylindrical bores in the contact elements.

5. An apparatus as set forth in claim 1 wherein the surface of each contact element is polished.

6. An apparatus as set forth in claim 1 wherein each contact element is adapted to be pushed on to a front end of one of the gripping elements.

7. An apparatus as set forth in claim 1 and further comprising means for connecting the gripping elements to form a pincer arrangement.

8. An apparatus as set forth in claim 4 wherein each of the bores in the contact elements is closed at one end.

9. An apparatus as set forth in claim 1 and further comprising means for fixing each contact element in its axial direction.

10. An apparatus as set forth in claim 1 wherein each of the contact elements is disposable.

11. An apparatus as set forth in claim 1 wherein the apparatus is disposable.

12. An apparatus as set forth in claim 1 wherein the mounting pins with the contact elements mounted rotatably thereon are disposable.

13. An apparatus for implanting an intraocular lens comprising:

first and second gripping elements having front ends which are movable towards each other for holding the intraocular lens therebetween for implanting; and at least one contact element mounted rotatably on each of the gripping elements;

the contact elements having increased thicknesses at their rear ends forming contact element regions of enlarged transverse dimensions relative to other regions of the contact elements between which the intraocular lens is held, the contact element regions defining peripheral flat surfaces of enlarged transverse dimensions, said peripheral flat surfaces producing an abutment action when they bear against each other and extending parallel to the axes of the contact elements, said abutment action preventing rotary movement of the contact elements when the intraocular lens is held between the other regions of the contact elements.

14. An apparatus as set forth in claim 13 wherein the contact elements are rotatably mounted by cylindrical mounting pins and matching cylindrical bores in the contact elements.

15. An apparatus as set forth in claim 13 wherein the surface of each contact element is polished.

16. An apparatus as set forth in claim 13 wherein each contact element is adapted to be pushed on to a front end of one of the gripping elements.

17. An apparatus as set forth in claim 13 and further comprising means for connecting the gripping elements to form a pincer arrangement.

18. An apparatus as set forth in claim 14 wherein each of the bores in the contact elements is closed at one end.

19. An apparatus as set forth in claim 13 and further comprising means for fixing each contact element in its axial direction.

20. An apparatus as set forth in claim 13 wherein each of the contact elements is disposable.

21. An apparatus as set forth in claim 13 wherein the apparatus is disposable.

22. An apparatus as set forth in claim 13 wherein the mounting pins with the contact elements mounted rotatably thereon are disposable.

* * * * *